US00PP29043P3

(12) United States Plant Patent
Kordes

(10) Patent No.: US PP29,043 P3
(45) Date of Patent: Mar. 6, 2018

(54) HYBRID TEA ROSE PLANT NAMED KORTALTAL

(50) Latin Name: *Rosa hybrida*
Varietal Denomination: KORtaltal

(71) Applicant: W. Kordes Söhne Rosenschulen GmbH & Co. KG, Klein Offenseth-Sparrieshoop (DE)

(72) Inventor: Tim-Hermann Kordes, Klein Offenseth-Sparrieshoop (DE)

(73) Assignee: W. Kordes Söhne Rosenschulen GmbH & Co. KG, Klein Offenseth-Sparrieshoop (DE)

( * ) Notice: Subject to any disclaimer, the term of this patent is extended or adjusted under 35 U.S.C. 154(b) by 22 days.

(21) Appl. No.: 14/999,143

(22) Filed: Apr. 1, 2016

(65) Prior Publication Data

US 2016/0330885 P1 Nov. 10, 2016

Related U.S. Application Data

(60) Provisional application No. 62/179,468, filed on May 8, 2015.

(51) Int. Cl.
*A01H 5/02* (2006.01)

(52) U.S. Cl.
USPC ..... Plt./130

(58) Field of Classification Search
USPC ..... Plt./130, 132, 134, 102, 104, 141, 143, Plt./145
CPC ..... A01H 5/0222; A01H 5/0216; A01H 5/02; A01H 5/00
See application file for complete search history.

(56) References Cited

PUBLICATIONS

Societe Francaise des Roses Results of the 84th Internationa Roses Competition Lyon News 2014, retrieved on Jun. 20, 2017, retrieved from the Internet at <https://societefrancaisedesroses.asso.fr/fr/archives/concours.htm> one page.*
Societe Francaise des Roses Google English translation 2017, one page.*
Pluto Plant Variety Database 20170620 retrieved on Jun. 20, 2017 for *Rosa* 'Kortaltal', retrieved from the Internet at <http://www.upov.int/pluto/en/index.jsp> one page.*

* cited by examiner

*Primary Examiner* — June Hwu
(74) *Attorney, Agent, or Firm* — Samuel R. McCoy, Jr.

(57) ABSTRACT

'KORtaltal' is a new and distinct variety of *Rosa hybrida* which is characterized by the combination of a compact and upright growth habit, dark green and glossy foliage, good resistance to common rose diseases, large yellow flowers with red petal margins, and flowers borne in small clusters. The new variety propagates successfully by stem cuttings and grafting and has shown to be uniform and stable in the resulting generations from asexual propagation.

1 Drawing Sheet

Latin name of genus and species: The Latin name of the genus and species of the novel variety disclosed herein is *Rosa hybrida.*

Variety denomination The inventive variety of *Rosa hybrida* disclosed herein has been given the variety denomination 'KORtaltal'.

BACKGROUND OF THE INVENTION

Parentage: The *Rosa hybrida* variety 'KORtaltal' is the result of a controlled cross-pollination breeding program carried out by the inventor in Klein Offenseth-Sparrieshoop, Germany. The objective of the said breeding program was to create a new and distinct rose plant with unique qualities, such as:

1. Uniform growth and flowering; and
2. Abundant recurrent flowers; and
3. Attractive yellow and red-margined flowers; and
4. Attractive and abundant foliage; and
5. Resistance to diseases encountered in landscapes and gardens.

This combination of qualities is not present in prior rose cultivars known to the inventor. These objectives have been substantially achieved and in that distinguish 'KORtaltal' from all other varieties known to the inventor.

'KORtaltal' is a seedling selection which resulted from the controlled pollination of *Rosa hybrida* 'TANeiglat' (not patented), the seed parent, and *Rosa hybrida* 'KORquelda' (U.S. Pat. No. 17,048), the pollen parent, during the summer of 2003. As part of a rose development program, Tim-Hermann Kordes germinated seeds from the aforementioned hybridization during the following winter and conducted evaluations and observations on the resulting seedlings in a controlled environment in Klein Offenseth-Sparrieshoop, Germany. The resulting seedlings exhibited distinctive physical and biological characteristics. The new rose plant was selected as a single plant in May of 2004 from the seedling beds due to its superior characteristics and asexually propagated for further evaluation. This new and distinctive rose variety was given the name 'KORtaltal'.

Asexual Reproduction: The first asexual propagation of 'KORtaltal' was performed in July of 2004 at the inventor's nursery in Offenseth-Sparrieshoop, Germany. Subsequently, 'KORtaltal' has been successfully propagated by stem cuttings and bud grafting in Jackson County, Oreg. These initial and other subsequent propagations conducted in controlled environments demonstrate that 'KORtaltal' reproduces true to type in successive generations of asexual reproduction.

SUMMARY OF THE INVENTION

The following characteristics have been repeatedly observed and represent the distinguishing characteristics of the new *Rosa hybrida* cultivar 'KORtaltal'. These traits, in combination, distinguish 'KORtaltal' as a new and distinct cultivar.

1. *Rosa hybrida* 'KORtaltal' exhibits a compact, upright growth habit; and
2. *Rosa hybrida* 'KORtaltal' exhibits dark green and glossy foliage; and
3. *Rosa hybrida* 'KORtaltal' exhibits good resistance to black spot disease, *Botrytis* and powdery mildew; and
4. *Rosa hybrida* 'KORtaltal' exhibits flowers borne in small clusters; and
5. *Rosa hybrida* 'KORtaltal' exhibits a large flower size for a hybrid tea rose; and
7. *Rosa hybrida* 'KORtaltal' exhibits yellow flowers with red petal margins.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORtaltal', taken from twelve month old plants.

DETAILED BOTANICAL DESCRIPTION

The following is a detailed botanical description of a new and distinct variety of *Rosa hybrida* known as 'KORtaltal', based upon observations made in August of 2015, from four year-old grafted plants grown outdoors in Jackson County, Oreg. Those skilled in the art will appreciate that certain characteristics will vary with older or, conversely, with younger plants. 'KORtaltal' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2001 edition except where common terms of color are used.

A botanical description of 'KORtaltal' and comparisons with other varieties of *Rosa hybrida* are provided below.

General plant description:

*Commercial classification.*—Hybrid tea rose.

*Growth rate.*—Moderate.

*Growth habit.*—Compact and upright.

*Mature dimensions.*—100 cm tall and 70 cm wide, on average.

*Cold hardiness.*—Grown successfully in USDA Hardiness Zone 6.

*Propagation.*—Stem cuttings and bud grafting.

*Disease resistance.*—Good resistance to powdery mildew (*Sphaerotheca pannosa* var. *rosae*), blackspot (*Diplocarpon rosae*) and rust (*Phragmidium mucronatum* and *P. tuberculatum*) diseases under normal growing conditions in Jackson County, Oreg.

Root system: Fibrous.

Stems:

*Stem color.*—Young stems are Yellow-Green Group 147C; mature stems are Yellow-Green Group 146C.

*Anthocyanin intonations.*—Greyed-Purple Group 184B intonations are present on young stems.

*Stem surface texture.*—Both young and mature stems exhibit a smooth texture.

*Stem dimensions.*—Typical mature stems are approximately 45 cm long and 4.5 to 7.0 mm in diameter.

*Prickles.*—Incidence — Present; 20 prickles per 10 cm of stem, on average. Size — Highly variable, with the largest prickles measuring 6 mm long and numerous small prickles ranging in size from 1 to 3 mm long. Immature prickle color — Greyed-Purple Group 185A. Mature prickle color — Greyed-Brown Group 189B. Anthocyanin intonations — None present. Shape — Larger prickles are concave and the smaller prickles are linear.

Leaves:

*Arrangement.*—Imparipinnate compound leaves; mature axillary leaves consisting of 5 to 7 leaflets. It is common to see leaves with both 5 and 7 leaflets.

*Attachment.*—Petiolate.

*Dimensions.*—150 mm long and 120 mm wide.

*Abundance.*—Average.

*Stipules.*—Size — 18 mm long and 5 mm wide. Stipule color — Yellow-Green Group 147C. Anthocyanin intonations — Greyed-Purple Group 184B. Anthocyanin intonations are strong in the central zone of the adaxial surface and the marginal zone of the abaxial surface. Stipitate glands — Abundant on the abaxial surface and the margins. Margins — Abundant stipitate glands. Texture, adaxial surfaces — Glabrous. Texture, abaxial surfaces — Papillate. Apex — Apiculate. Base — Winged.

*Petiole.*—Length — Average 30 mm. Diameter — Average 2 mm. Petiole color, adaxial and abaxial surfaces — Yellow-Green Group 145A. Margins — Entire with a limited number of stipitate glands. Anthocyanin intonations — Greyed-Purple Group 184B on stipitate glands, margins, adaxial surface of the midrib and occasionally on the abaxial surface. Prickles — Small prickles are occasionally present on the abaxial surface. Stipitate glands — Abundant; present on the margins and abaxial surface. Texture — Papillate. Strength — Strong.

*Rachis.*—Length — Average 22 mm. Diameter — Average 1.5 mm. Color — Yellow-Green Group 145A. Anthocyanin intonations — Greyed-Purple Group 184B on the adaxial surface, margins, stipitate glands, and prickles; occasionally present on the abaxial surface. Margins — Entire; limited number of stipitate glands are present. Prickles — A few small prickles on the abaxial surface. Stipitate glands — Limited number present along margins and abaxial surface. Pubescence — Abundant fine white hairs on the upper surface. Texture — Papillate.

*Leaflets.*—Quantity — Leaves with both 5 and 7 leaflets are regularly observed. Dimensions — Average size of the terminal leaflet is 55 mm long and 40 mm wide. Shape — Elliptic. Apex — Acuminate.

Base — Obtuse. Margins — Serrated; a slight undulation is occasionally present. Luster and texture, adaxial surface — Semi-glossy and smooth. Luster and texture, abaxial surface — Matte and leathery. Juvenile foliage color, adaxial surface — Yellow-Green Group 146A. Juvenile foliage color, abaxial surface — Yellow-Green Group 146C. Mature foliage color, adaxial surface — Yellow-Green Group 146A. Mature foliage color, abaxial surface — Yellow-Green Group 146C. Anthocyanin intonations — Greyed-Purple Group 185A is present on the margins, midrib, and veins of the adaxial surface and all of the abaxial surface. These intonations are present in both juvenile and mature foliage; intonations are stronger on juvenile foliage. Venation — Reticulate. Petiolule — Dimensions — 5 mm long and 1 mm in diameter. Petiolule color, adaxial surface — Greyed-Purple Group 184B. Petiolule color, abaxial surface — Yellow-Green Group 145B. Prickles — None present. Texture, adaxial and abaxial surfaces — Smooth. Margins — Entire, with limited number of stipitate glands.

Inflorescence:

*Inflorescence type.*—Corymbs; occasionally flowers are solitary. Flowers are held upright.

*Blooming habit.*—Recurrent; floriferous.

*Quantity of flowers.*—Generally three to five flower buds per inflorescence.

*Size.*—25 cm tall and 9 cm wide, on average.

*Peduncle.*—Length — 15 to 25 mm average length. Diameter — 2 to 4 mm average diameter. Color — Yellow-Green Group 147A. Anthocyanin intonations — Greyed-Purple Group 185B. Strength — Strong. Texture — Smooth with stipitate glands. Pubescence — Glabrous.

Flowering laterals: Absent.

Bud:

*Bud form.*—Short; globular.

*Size.*—Upon opening, 25 mm in length from base of receptacle to distal end of bud and 20 mm diameter at its widest point.

*Texture.*—Smooth.

*Color, as sepals first unfold.*—Green-Yellow Group 1C at the base, with margins that are a combination of Red Group 46B to Red Group 46D.

*Color when one-quarter open, inner side.*—Marginal zone — Yellow-Orange Group 14A, with intonations of Red Group 39A. Middle zone — Yellow-Orange Group 20A. Basal zone — Yellow-Orange Group 14B.

*Color when one-quarter open, outer side.*—Marginal zone — Yellow-Orange Group 16C to 16D. Middle zone — Yellow-Orange Group 15A. Basal zone — Yellow-Orange Group 16C to 16D; margins are Red Group 46B.

Flower:

*Pedicels.*—Surface — Glabrous with numerous stipitate glands. Length — 16 to 30 mm, on average. Diameter — 2 to 4 mm, on average. Color — Yellow-Green Group 146A. Anthocyanin intonations — Greyed-Purple Group 185C. Strength — Strong.

*Calyx.*—General — Comprised of five polysepalous sepals, with moderate foliaceous appendages present on three of the five sepals. Diameter of calyx — 60 mm, at anthesis. Sepals — Color, upper surface — Yellow-Green Group 146C with intonations of Greyed-Purple 185D in the middle and on the margin. Color, lower surface — Yellow-Green Group 146C with intonations of Greyed-Purple 185B on margins. Size — 20 to 25 mm long and 8 mm wide, on average. Apex — Apiculate. Base — Flat at union with receptacle. Quantity — Five. Upper surface — Strongly pubescent. Lower surface — Coriaceous, with an abundance of stipitate glands. Margins — With an abundance of stipitate glands.

*Corolla.*—General shape of corolla — Cupped to open; shallow. Shape of corolla when viewed from the side — Upon opening, upper portion — Flat. Upon opening, lower portion — Flattened convex. Open flower, upper portion — Flattened convex. Open flower, lower portion — Concave. Dimensions — Medium size for a hybrid tea rose. When open, the average flower diameter is 80 mm and the average flower height is 15 mm. Fragrance — Moderate; classic rose fragrance with a fruity scent. Duration — On the plant for 4 to 5 days; as a cut flower, flowers will last 4 to 5 days. Senesced petals drop away cleanly. Petals — Petal count — Exhibits double flowers with an average of 30 petals under normal conditions. Petal reflex — Petals are somewhat reflexed. Timing of petal reflex — Simultaneous. Petal margin — Entire to emarginate. Petal shape — Obovate. Apex — Obtuse. Base — Obtuse. Dimensions — 40 mm long and 40 mm wide. Texture, inner surface — Smooth. Texture, outer surface — Smooth. Petal color, upon opening — Outermost petals, inner surface — Marginal zone — Red Group 45C. Middle zone — Yellow Group 12C. Basal zone — Yellow Group 12B. Outermost petals, outer surface — Marginal zone — Orange-Red Group 33C. Middle zone — Yellow Group 12B to 12C, with intonations of Orange-Red Group 33C. Basal zone — Yellow Group 12A. Innermost petals, inner surface — Marginal zone — Yellow-Orange Group 15A. Middle zone — Yellow-Orange Group 15A. Basal zone — Yellow-Orange Group 15A. Innermost petals, outer surface — Marginal zone — Yellow-Orange Group 15A. Middle zone — Yellow-Orange Group 15A. Basal zone — Yellow-Orange Group 15A. Basal petal spots, upon opening — No distinct coloration at the petal base. Petal color, after opening — Outermost petals, inner surface — Marginal zone — Orange-Red Group 32D and margined Orange-Red Group 32B. Middle zone — Yellow Group 5C. Basal zone — Yellow Group 5A. Outermost petals, outer surface — Marginal zone — Orange-Red Group 32D and margined Orange-Red Group 32B. Middle zone — Yellow-Orange Group 14C, with intonations of Orange Group 29D. Basal zone — Yellow-Orange Group 14B. Innermost petals, inner surface — Marginal zone — Yellow Group 13B, with slight intonations of Orange Group 29D. Middle zone — Yellow Group 13B. Basal zone — Yellow Group 13B. Innermost petals, outer surface — Marginal zone — Yellow-Orange Group 14C, with slight intonations of Orange Group 29D. Middle zone — Yellow-Orange Group 14D. Basal zone — Yellow Group 13B. Basal petal spots, after opening — No distinct coloration at the petal base.

General Tonality — On open flower, Yellow-Orange Group 14C. Not fading. Petaloids — Quantity — 4 petaloids per flower, on average. Dimensions — Approximately 15 to 18 mm long and 5 to 7 mm wide. Color, inner surface — Yellow Group 13B. Color, outer surface — Yellow Group 13B. Margins — Indented. Shape — Varies from spatulate to elliptical. Apex — Acute to obtuse. Base — Attenuate to cuneate. Texture, inner and outer surfaces — Smooth.

Reproductive organs:

*Stamens.*—Quantity — Approximately 50, on average, and regularly arranged around the styles. Anthers — Shape — Reniform. Dimensions — 2 mm long and 1 mm wide, on average. Color — Yellow-Orange Group 17C. Pollen — Abundant. Color is Greyed-Orange Group 163B. Filaments — Color — Yellow-Orange Group 17C. Length — 10 mm.

*Pistils.*—Quantity — Abundant; approximately 60. Stigmas — Dimensions — 1 mm long and 1 mm wide. Location — Inferior in position to anthers. Color — Greyed-Yellow Group 162B. Styles — Length — Approximately 2.5 mm long. Color — Yellow-Green Group 145D, with intonations of Red Group 36B at the tip.

*Ovary.*—Dimensions — 8 mm long and 9 mm in diameter. Color — Yellow-White Group 158C.

*Receptacle.*—Shape — Funnel-shaped; occasionally urn-shaped. Dimensions — Approximately 10 mm high and 9 mm wide. Surface texture and pubescence — Smooth, with a few stipitate glands at the top. Color — Yellow-Green Group 146B. Texture — Glabrous.

Hips and seed formation:

Not observed to date.

COMPARISONS WITH THE PARENTS

The new rose plant may be distinguished from its seed parent, *Rosa hybrida* 'TANeiglat', by the following combination of characteristics:

1. 'KORtaltal' exhibits yellow flowers with red petal margins, whereas 'TANeiglat' exhibits cream-white flowers with red margins.
2. 'KORtaltal' exhibits flowers borne in small clusters, whereas 'TANeiglat' exhibits mostly solitary flowers.
3. 'KORtaltal' exhibits good disease resistance, whereas 'TANeiglat' exhibits only average disease resistance.

The new rose plant may be distinguished from its pollen parent, *Rosa hybrida* 'KORquelda', by the following combination of characteristics:

1. 'KORtaltal' exhibits a moderate rate of growth and compact habit, whereas 'KORquelda' exhibits a tall plant height with a vigorous rate of growth.
2. 'KORtaltal' exhibits shallow cup-shaped flowers, whereas 'KORquelda' exhibits flowers with a flattened appearance.
3. 'KORtaltal' exhibits good disease resistance, whereas 'KORquelda' exhibits very good disease resistance.

COMPARISON WITH THE MOST SIMILAR *ROSA* CULTIVAR KNOWN TO THE INVENTOR

For a comparison, several physical characteristics of the *Rosa hybrida* variety 'KORamflusa', a rose variety from the same inventor which is described and illustrated in U.S. Plant Pat. No. 24,406, are compared to 'KORtaltal' in Chart 1.

CHART 1

| Characteristic | 'KORtaltal' | 'KORamflusa' |
|---|---|---|
| General tonality of the flower, at anthesis. | Yellow-Orange Group 14C. | Yellow Group 13C and Yellow-Orange Group 16A. |
| Average diameter of the corolla, at anthesis. | 70 mm. | 60 mm. |
| Inflorescence type. | Corymb; small clusters of 3 to 5 flowers. | Panicle with up to 10 flowers. |

That which is claimed:

1. A new and distinct variety of rose plant named 'KORtaltal', as described and illustrated herein.

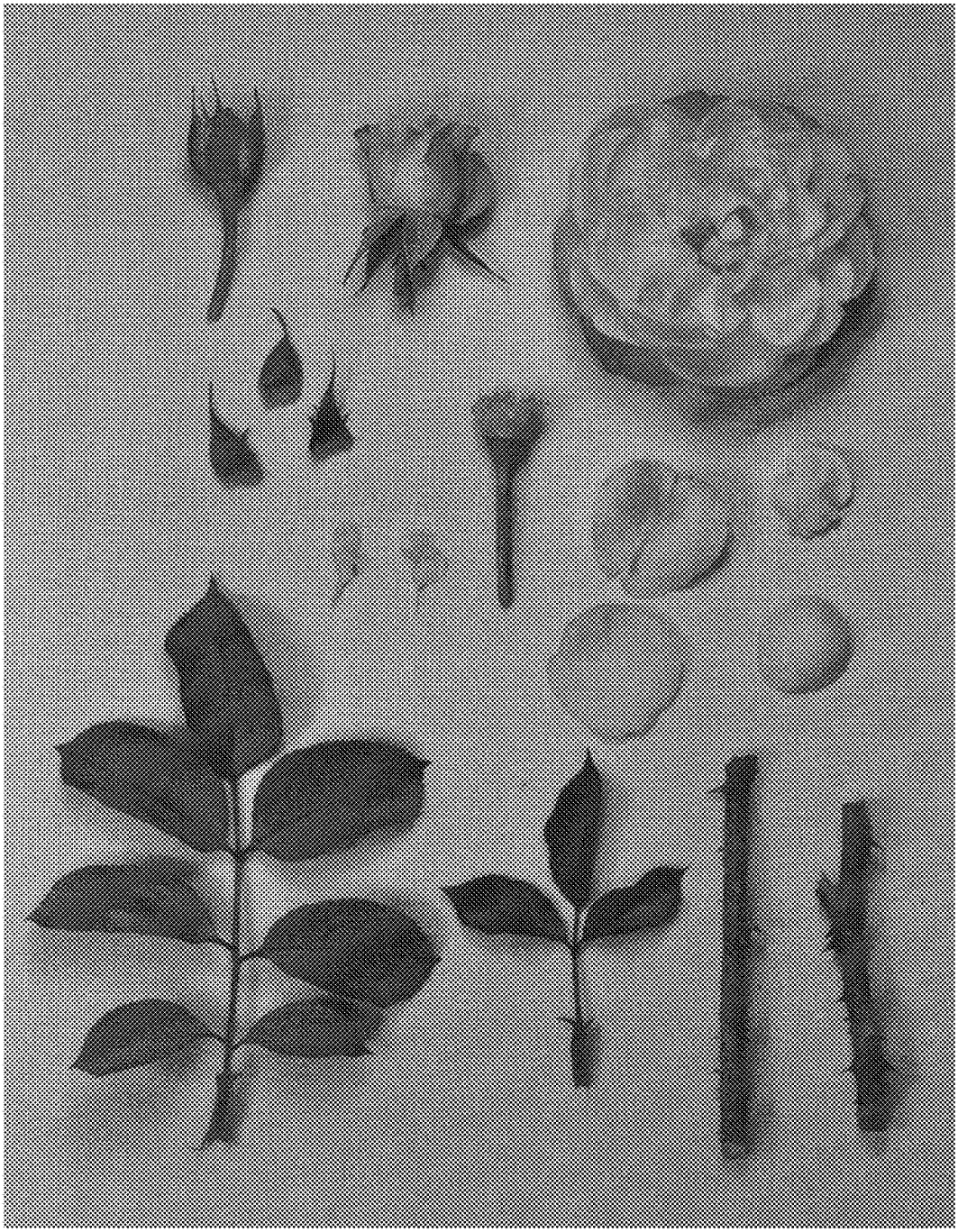

* * * * *